United States Patent [19]
Miles et al.

[11] Patent Number: 6,100,084
[45] Date of Patent: Aug. 8, 2000

[54] MICRO-SONICATOR FOR SPORE LYSIS

[75] Inventors: Robin R. Miles, Livermore; Phillip Belgrader, Manteca; Shanavaz L. Nasarabadi, Livermore, all of Calif.

[73] Assignee: The Regents of the University of California, Oakland, Calif.

[21] Appl. No.: 09/187,162

[22] Filed: Nov. 5, 1998

[51] Int. Cl.[7] .................................................. C12M 1/33
[52] U.S. Cl. .................................. 435/306.1; 435/286.7; 435/820; 366/114; 241/2
[58] Field of Search ..................... 366/114, 115; 241/2; 435/286.7, 820, 306.1; 436/175

[56] References Cited

U.S. PATENT DOCUMENTS

| | | |
|---|---|---|
| 3,851,861 | 12/1974 | Cummins et al. . |
| 4,026,765 | 5/1977 | Soper, Jr. . |
| 4,983,523 | 1/1991 | Li et al. .................................. 435/173 |
| 5,374,522 | 12/1994 | Murphy et al. .............................. 435/6 |
| 5,646,039 | 7/1997 | Northrup et al. .................... 435/287.2 |
| 5,837,303 | 11/1998 | Hayden ................................... 426/237 |

*Primary Examiner*—David A. Redding
*Attorney, Agent, or Firm*—L. E. Carnahan; Alan H. Thompson

[57] ABSTRACT

A micro-sonicator for spore lysis. Using micromachining technology, the micro-sonicator uses ultrasonic excitation of spores to perform spore and cell lysis. The micro-sonicator comprises a container with a cavity therein for retaining the sample in an ultrasonic transmission medium, the cavity being closed by a silicon membrane to which an electrode and piezoelectric material are attached, with the electrode and piezoelectric material being electrically connected to an AC signal generator which causes the membrane to flex and vibrate at the frequency of the applied voltage.

18 Claims, 1 Drawing Sheet

MICRO-SONICATOR FOR SPORE LYSIS

The U.S. Government has rights in this invention pursuant to Contract No. W-7405-ENG-48 between the U.S. Department of Energy and the University of California for the operation of Lawrence Livermore National Laboratory.

BACKGROUND OF THE INVENTION

The present invention relates to spore and cell lysis, particularly to the use of ultrasonic excitation to lyse spores, and more particularly to a micro-sonicator for spore and cell lysis.

Detection of pathogens using DNA analysis requires extraction of the DNA from the host spore or cell. Recently, the use of ultrasonic excitation to lyse (losing or dissolving) spores has been demonstrated. The present invention further advances the use of ultrasonic excitation to lysis of spores and cells in a micro-fluidic system. This is accomplished by a micro-sonicator to perform this function using micromachining technology. The micro-sonicator of the present invention involves a cavity containing ultrasonic transmission media in which a spore or cell sample is contained, with the cavity being closed by a flexible member having a patterned electrode and piezoelectric material formed thereon. An AC voltage is applied which causes the membrane to flex and vibrate at the frequency of the applied voltage.

SUMMARY OF THE INVENTION

It is an object of the present invention to provide a micro-sonicator for spore or cell lysis.

A further object of the invention is to provide a micro-sonicator for cell lysis for PCR analysis for clinical genetic testing.

Another object of the invention is to provide a mini-sonicator for spore and cell lysis using ultrasonic excitation of the spore or cell fabricated using micromachining technology.

Another object of the invention is to provide a miniature ultrasonic excitation device for detection of pathogens using DNA which requires extraction of the DNA from the host spore or cell.

Another object of the invention is to provide a mini-sonicator to perform extraction of the DNA from host spores or cells in a micro-fluidic system.

Other objects and advantages of the present invention will become apparent from the following description and accompanying drawings. The invention is a micro-sonicator for spore or cell lysis. The micro-sonicator can be fabricated using micromachining technology, and can be utilized for the extraction of DNA from the host spore or cell in a micro-fluidic system. Basically, the micro-sonicator comprises a container having a cavity therein containing an ultrasonic transmission media and in which a spore or cell is positioned, with the cavity being closed by a flexible membrane having a patterned electrode and a piezoelectric material. An AC voltage is applied to the piezoelectric material, which causes the membrane to flex and vibrate at the frequency of the applied voltage.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

The present invention is directed to a micro-sonicator for spore and cell lysis using ultrasonic excitation. The micro-sonicator is fabricated using micromachining technology and lyse spores and cells in a micro-fluidic system. Basically, the micro-sonicator comprises a container having a cavity therein for retaining a spore or cell in an ultrasonic transmission media, and the cavity is closed by a membrane on which is formed an electrode and a layer of piezoelectric material electrically connected to an AC voltage source. The spores or cells may be placed directly in the cavity or they can be enclosed in a plastic container which may be part of a fluidic circuit. Beads can be added to the spore or cell solution to aid in sonication. When an AC voltage is applied to the piezoelectric material, such causes the material to flex and vibrate the membrane at the frequency of the applied voltage. Vibration of the membrane causes ultrasonic excitation of the spores or cells in the cavity via the ultrasonic transmission material therein.

Figure 1:
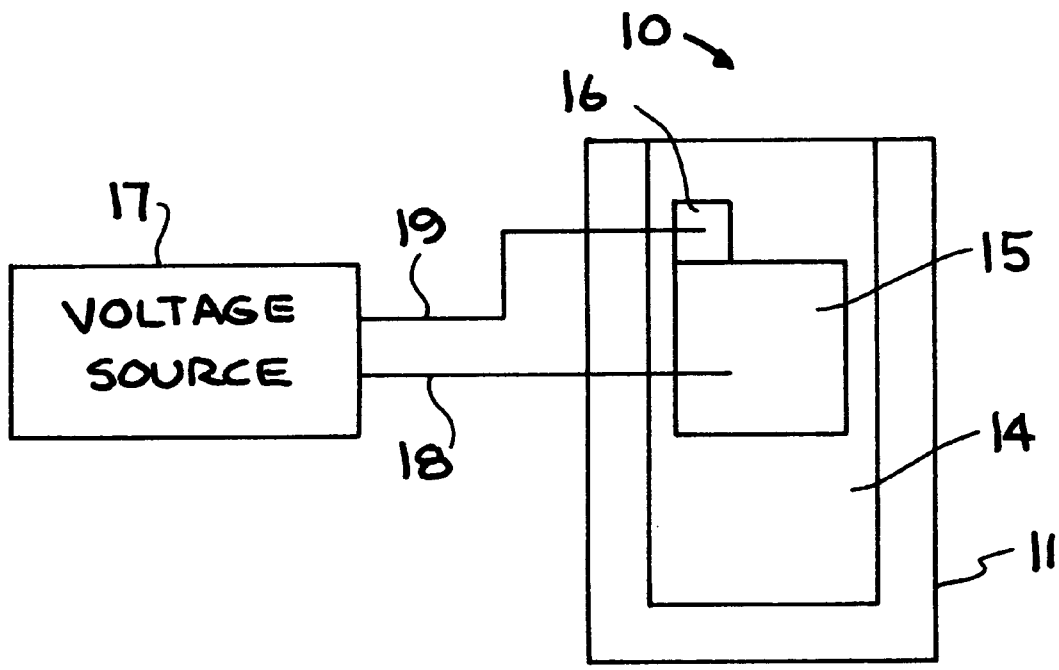
FIG. 1 is a view of an embodiment of a micro-sonicator made in accordance with the present invention.
Figure 2:
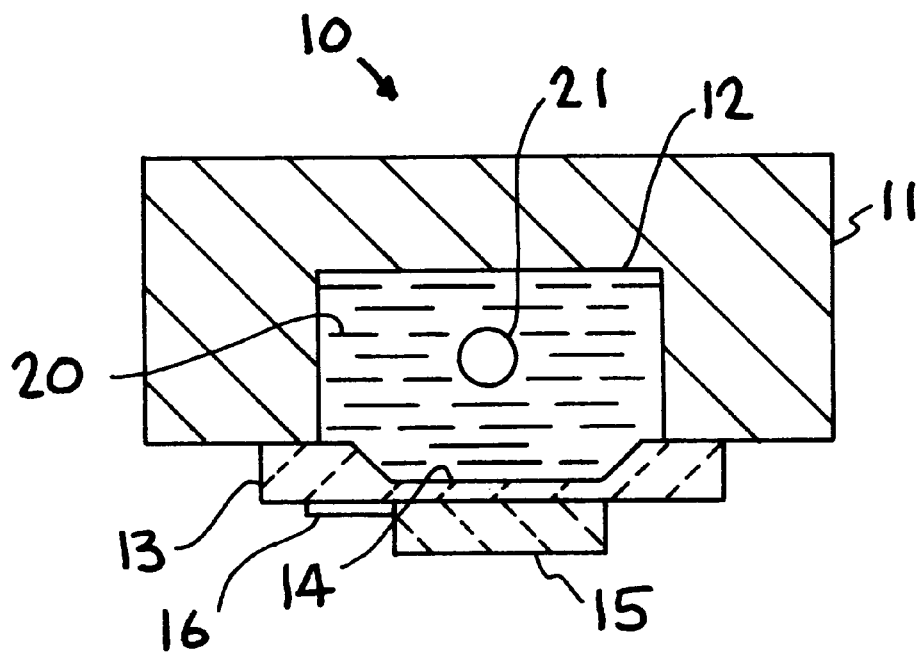
FIG. 2 is a cross-sectional view of the micro-sonicator of FIG. 1.

Referring now to the drawings, the device or embodiment of the micro-sonicator, generally indicated at 10, comprises a container 11 having a cavity 12 over which is removably positioned a member 13 having a thin section forming a membrane 14. A layer 15 of bi-morph piezoelectric material, such as PZT, is secured to the membrane 14, such as by soldering, and an electrode 16 is formed on the membrane adjacent the piezoelectric layer 15 using photolithographic techniques. Electrical connections to the piezoelectric material can otherwise be made through the use of bonding or soldering of wires. An AC voltage source 17 is connected by leads 18 and 19 to the piezoelectric layer 15 and the electrode 16. As shown in FIG. 2, the cavity 12 contains ultrasonic transmission media 20, such as water or ultrasonic gel; and a spore or cell sample 21, contained in a plastic is located in the cavity 12. When an AC voltage or signal produced by source 17 is applied to the piezoelectric layer 15, it causes the material 15 to flex and vibrate the membrane 14 at the frequency of the applied voltage. This, in turn, produces ultrasonic excitation of the transmission media 20 causing lysis of the spore or cell sample 21.

By way of example, the container 11 may be constructed of aluminum or other metals, ceramics such as $AlO_3$, or plastic, bakelite, polycarbonate and polypropylene; with the cavity 12 having a depth of 0.025 to 2.0 inch, width of 0.025 to 2.0 inch, and length of 0.25 to 2.0 inch; the member 13 may be composed of silicon, glass, or stainless steel, or ceramic, such as $AlO_3$; and the membrane 14 may, for example, be etched in the silicon member 13, or otherwise formed to have a thickness of 0.0005 to 0.10 inch; the bi-morph piezoelectric layer 15, in addition to being formed of PZT, may be composed of quarts or BaTi, with a thickness of 0.0005 to 0.10 inch, length of 0.05 to 1.0 inch, and width of 0.05 to 1.0 inch; while the electrode 16 may be composed of Au, Pt, or Al, with a thickness of 100 Å to 0.010 inch, length of 0.05 to 1.0 inch, and width of 0.05 to 1.0 inch. The AC source 17 may be constructed to produce a signal having a frequency of 5 KHz to 2 MHz and a voltage of up to 1000 V.

It has thus been shown that the present invention provides a micro-sonicator for spore and cell lysis and may be utilized in a micro-fluidic system. Lysis of spores and cells is used, for example, for counter biological warfare applications to break open potential pathogens to extract DNA for analysis; and cell lysis is used for PCR analysis for clinical genetic tests; and thus this invention enables miniaturization of such existing systems for the lysis of spores and cells.

While a particular embodiment of the invention has been described and illustrated, along with particular materials and parameters, such are not intended to be limiting. Modifications and changes may become apparent to those skilled in the art and it is intended that the invention be limited only by the scope of the amended claims.

What is claimed is:

1. A micro-sonicator for spore or cell lysis, comprising:
   a container having a cavity therein adapted to contain spore or cell samples,
   a quantity of ultrasonic transmission media in said cavity,
   at least a membrane positioned to cover said cavity,
   piezoelectric material positioned on said membrane, and
   means for causing flexing of said piezoelectric material and vibration of said membrane thereby causing ultrasonic excitation of the transmission media adapted to cause lysis of spore or cell samples in said cavity.

2. The micro-sonicator of claim 1, wherein said container is constructed of material selected from the group consisting of aluminum, ceramics, plastics, bakelite, polycarbonate, and other metals.

3. The micro-sonicator of claim 1, wherein said membrane is constructed of material selected from the group consisting of silicon, glass, ceramics, and stainless steel.

4. The micro-sonicator of claim 1, wherein said membrane has a thickness in the range of 0.0005 to 0.10 inch.

5. The micro-sonicator of claim 1, additionally including a member positioned to cover said cavity, said member including a thin section defining said membrane.

6. The micro-sonicator of claim 5, wherein said member is composed of silicon, glass, ceramics, and stainless steel.

7. The micro-sonicator of claim 1, wherein said piezoelectric material is positioned only on a section of said membrane.

8. The micro-sonicator of claim 1, wherein said piezoelectric material is selected from the group consisting of PZT, barium titanate and quartz.

9. The micro-sonicator of claim 1, wherein said means includes an electrode located on said membrane, and an AC power source.

10. The micro-sonicator of claim 9, wherein said electrode is formed on a surface of said membrane.

11. The micro-sonicator of claim 1, in combination with a spore or cell sample, positioned in said cavity for lysis by ultrasonic excitation of said sample, whereby said means causes said piezoelectric material to flex and vibrate said membrane at a frequency produced by said means.

12. The combination of claim 11, wherein said means include an AC voltage source, and wherein said frequency is the frequency of the applied voltage from the AC voltage source.

13. The combination of claim 11, wherein said spore or cell is enclosed in a plastic container.

14. The combination of claim 1, additionally including beads located in said cavity to aid sonication.

15. In a micro-fluidic system, the improvement comprising:
   a micro-sonicator for spore and cell lysis using ultrasonic excitation of the spore or cell, said micro-sonicator including a container having a cavity therein and containing ultrasonic transmission media, a membrane positioned over said cavity, and means for causing vibration of said membrane producing ultrasonic excitation of spore or cell located in said cavity.

16. The improvement of claim 15, wherein said membrane constitutes a thin portion of a member positioned to cover said cavity.

17. The improvement of claim 15, wherein said means includes a piezoelectric material and an electrode located on a surface of said membrane.

18. The improvement of claim 17, wherein said means additionally includes an AC power supply connected to said piezoelectric material and said electrode, whereby an AC voltage applied to said piezoelectric material causes the material to flex and vibrate the membrane at a frequency of the applied voltage, causing the ultrasonic excitation of the spores or cells in said cavity via said ultrasonic transmission media.

* * * * *